United States Patent [19]
Ellis et al.

[11] 3,943,174
[45] Mar. 9, 1976

[54] BISULFITE REACTION WITH OLEFINS

[75] Inventors: Robert J. Ellis; Lawrence H. Shepherd, Jr.; Richmond M. Starrett, all of Baton Rouge, La.

[73] Assignee: Ethyl Corporation, Richmond, Va.

[22] Filed: Mar. 4, 1974

[21] Appl. No.: 448,039

[52] U.S. Cl. .............................................. 260/513 B
[51] Int. Cl.² ....................................... C07C 139/12
[58] Field of Search ............................... 260/513 B

[56] References Cited
UNITED STATES PATENTS

| | | | |
|---|---|---|---|
| 2,504,411 | 4/1950 | Harman | 260/513 B |
| 2,653,970 | 9/1953 | Fessler | 260/513 B |
| 2,671,800 | 3/1954 | Copenhaver | 260/513 B |
| 3,084,186 | 4/1963 | Clippinger | 260/513 B |
| 3,168,555 | 2/1965 | Clippinger et al. | 260/513 B |
| 3,231,606 | 1/1966 | Fessler | 260/513 B |
| 3,306,931 | 2/1967 | Adams et al. | 260/513 B |
| 3,356,717 | 12/1967 | Furrow | 260/513 B |
| 3,479,397 | 11/1969 | Norton et al. | 260/503 |
| 3,558,693 | 1/1971 | Rein et al. | 260/513 B |
| 3,579,546 | 5/1971 | Norton | 260/513 B |
| 3,706,791 | 12/1972 | Robinette | 260/513 B |

*Primary Examiner*—James O. Thomas, Jr.
*Assistant Examiner*—Nicky Chan
*Attorney, Agent, or Firm*—Donald L. Johnson; John F. Sieberth; Shelton B. McAnelly

[57] ABSTRACT

A process is disclosed for producing alkyl sulfonates by the addition of bisulfite ions to olefinic double bonds. In the process, ammonium, or alkali metal bisulfite and olefins having from about 8 to about 30 carbon atoms per molecule are reacted in the presence of lower alkanol having from 2 to about 4 carbon atoms, water and a reaction initiating agent.

22 Claims, No Drawings

BISULFITE REACTION WITH OLEFINS

BACKGROUND OF THE INVENTION

1. Field of the Invention

The invention relates to the preparation of alkyl sulfonates by the addition of bisulfite to olefin. The product of the reaction has surface active properties and can be used for cleansing various materials; e.g., fabrics, skin and hard surfaces such as dishes.

2. Description of the Prior Art

The reaction of olefins with bisulfite ions to produce sulfonic acid salts has been known for a long time; however, the prior art is contradictory and appears to teach that it is necessary to use complicated procedures that are time consuming and inconvenient.

In U.S. Pat. No. 2,504,411 it was disclosed that organic peroxides and peresters such as tertiary butyl perbenzoate are preferred initiators. Typical Example III of U.S. Pat. No. 2,504,411 described a process apparently similar to that of Example I of U.S. Pat. No. 3,084,186 which the latter indicates to be virtually inoperative. As a result, in U.S. Pat. No. 3,084,186 provides a process which requires progressive addition of the bisulfite at such a rate as to maintain an amount of unreacted bisulfite ion within the range of 0.05 to 0.25 mol per mol of olefin originally introduced. It is evident that this requires initiating the reaction with only a small percentage of the necessary bisulfite and also requires the subsequent progressive addition of most of the bisulfite needed for the reation. The process was described in the patent as requiring visual observation or periodic analysis of the reaction mixture to determine bisulfite content to indicate when to add the bisulfite in the course of the reaction. Since such observation and analysis as well as the control operations are more or less subjective or time consuming, it would be desired to have a workable process which does not require one to start a run with a small initial amount of bisulfite and then have to add most of the bisulfite during the course of the reaction based on the maintenance of an analytically determined bisulfite concentration. On the other hand, some of the prior art discloses that the process is of low conversion, such as 75 percent or less and requires a large excess of bisulfite. Since excess bisulfite remains as a contaminant of the product, it is desired to provide a process that does not require excess bisulfite.

SUMMARY OF THE INVENTION

The present invention provides a bisulfite reaction process which does not require progressive addition of most of the bisulfite. In the present process, substantially all of the bisulfite reactant necessary is suitably combined initially with the olefin and pH is controlled by adding $SO_2$ during the reaction providing a high yield process that proceeds rapidly with high conversion of the olefin and with minimum production of molecules having two sulfur atoms each. Simple pH measurement and the addition of a small amount of $SO_2$ is the principal measurement and control required for the present process without need for either visual observation of the reaction mass or for analysis of samples of the reaction mixture for bisulfite content.

The present invention teaches that vinyl olefins having from about 8 to about 30 carbon atoms per molecule will react with ammonium or alkali metal bisulfite at a temperature of from about 25° to about 200°C in the presence of an effective amount of suitable reaction initiator.

An important aspect of the present invention is the use of solvent as herein defined. Another important aspect is the control of the pH to maintain a pH of from about 5 to about 8. Temperature and pressure are important in connection with rate but they are not unduly critical. In general, one usually prefers operation at reflux at about atmospheric pressure while avoiding costly high vacuum or high pressure equipment. Although various useful reactants and solvents have different physical properties such as melting point, boiling point, decomposition temperature, and the like, useful temperatures range from about 25°C to about 200°C and useful pressures are from about ½ to about 15 atmospheres.

Accordingly, the present invention relates to a process for preparing alkyl sulfonate salts which comprises reacting from about 1.0 to about 1.7 mols of aqueous ammonium or alkali metal bisulfite with about 1.0 mol of straight chain terminal olefin having from about 8 to about 30 carbon atoms per molecule in the presence of lower alkanol having from 2 to about 4 carbon atoms per molecule and an effective amount of reaction initiating agent, at a pH of from about 5 to about 8, at a temperataure of from about 25° to about 200°C, the reaction system containing from about 70 to about 95 wt. percent of water and lower alkanol, the weight ratio of alkanol to water ranging from about 1:4 to about 3:1, the initial pH of the reaction mixture being from about 5 to about 8, $SO_2$ being fed to the system as the reaction progresses to maintain a selected pH of from about 5 to about 8.

Preferably the amount of the solvent is from about 75 to about 85 weight percent of the reaction system, and typically is about 80 percent of the reaction system.

Preferably the weight ratio of alkanol to water is from about 1:3 to about 1:1, and typically it is about 2:3.

Preferably the mol ratio of busulfite to olefin is from about 1:1 to about 1.50:1, and typically it is from about 1.30:1 to about 1.45:1.

Preferably the temperature used for the reaction is from about 40° to about 120°C, especially from about 80° to about 90°C.

Preferably the initiator is an organic peroxide, especially a tertiary alkyl perester. Especially preferred initiators are tertiary alkyl perbenzoates and peracetates, typically tertiary butyl perbenzoate and tertiary butyl peracetate.

Preferably the bisulfite is sodium bisulfite, sodium metabisulfite or ammonium bisulfite or a mixture thereof, especially a mixture of sodium bisulfite and sodium metabisulfite.

Preferably the pH is from about 6 to about 7.5. In a preferred aspect, the initial pH is from about 5 to about 7 and $SO_2$ is added as the reaction proceeds to maintain a pH not in excess of about 7.5.

Preferably substantially all of the reactants, the water, the initiator and the solvent are combined and then the system is heated to reflux at the selected temperature and pressure for the reaction.

Preferably the pressure of operation is at about atmospheric pressure.

In a preferred aspect of the present invention, a process is provided for preparing alkyl sulfonate salts which comprises producing a reaction mixture containing the addition product of ammonium or alkali metal bisulfite and straight chain terminal olefins having from about 8 to about 30 carbon atoms per molecule, water, and lower alkanol having from 2 to about 4 carbon atoms per molecule, the system containing from about 70 to about 95 wt. percent of water and lower alkanol, the weight ratio of alkanol to water ranging from about 1:4 to about 3:1, withdrawing intermittently or continuously a portion of the reaction mixture, and replacing the withdrawn reaction mixture with additional bisulfite, olefin, water, alcohol and reaction initiating agent to maintain said proportions of bisulfite while maintaining a pH of from about 5 to about 8 and a temperature of from about 25° to about 200°C.

Preferably the withdrawal and replacement are proportioned to maintain a homogeneous system.

In the present process, the manner of feed of the bisulfite is not critical or complicated. Preferably, substantially all of the bisulfite required for conversion of the vinylic olefin bonds is charged to the reaction vessel at the start. Several phases may result from such an addition but for the most part the system contains only two phases, both of which are liquid, and rapid reaction rates and high conversion of olefin prevail particularly when good agitation is provided and oxygen is excluded. This result is surprising in view of the express teaching in U.S. Pat. No. 3,084,186 that the feed of the bisulfite in a progressive manner is required and that presence of substantially all of the required bisulfite at the start produces a substantially inoperative process.

Olefins used in the process are preferably straight chain terminal monoolefins having from about 8 to about 30 carbon atoms per molecule. Preferably the olefins have from about 10 to about 20 carbon atoms per molecule. Typical olefins are decene-1, undecene-1, dodecene-1, tridecene-1, tetradecene-1, pentadecene-1, hexadecene-1, heptadecene-1, octadecene-1, nonadecene-1, and eicosene-1. Other olefins useful are acyclic terminal olefins having remote branching at or beyond the gamma carbon atom such as 3-ethyl dodecene-1, 4-methyl dodecene-1 and the like. The process may be performed with various pure olefins or with mixtures containing olefins of two or more different molecular weights. Thus in various typical situations, a 1:1:1 or a 1:2:1 or a 2:1:2 or a 65:25:10 weight ratio mixture of dodecene-1, tetradecene-1 and hexadecene-1 or a 1:1 or 2:1 or 1:2 weight ratio mixture of dodecene-1 and tetradecene-1, or a 1:1 weight ratio mixture of dodecene-1 and hexadecenee-1, typically obtained by suitable processes such as fractionation of wide range mixtures and/or blending of cuts or individual olefins may be reacted, or the typical individual olefins, such as dodecene-1, tetradecene-1 and hexadecene-1, may be reacted to provide desired sulfonate compositions for use or to provide sulfonate blending stock for mixing in various combinations and proportions. Thus convenient feed streams and commercially available olefins can be utilized in various ways to produce products of desired molecular weight distributions. In general, the olefinic bonding which is between a carbon atom that carries two hydrogens and a carbon atom that carries one hydrogen reacts selectively in the process and reaction of vinylidene and internal olefinic bonds is substantially avoided. The product sulfonates thus have little or no branching of the carbon skeleton or have only remote branching and substantially all molecules carry a sulfur containing radical linked at a terminal carbon atom. Where internal or vinylidene ($\beta$-branched) olefinic bonds are present in feed olefins, they normally do not react to any substantial extent. It will be appreciated, however, that where reaction of internal or vinylidene olefins is desired, that one may prefer to use higher temperature to promote such reaction. In general, such higher temperature will not exceed 200°C. Mono olefins with unreactive olefinic bonds remain as diluent to be removed, where desired, from the product after the reaction, typically by distillation or by solvent extraction with a suitable solvent, preferably a hydrocarbon such as pentane, hexane, hexene, etc. Typically the reaction solvent is removed by evaporation. In general, it is desired to avoid large amounts of unreactive hydrocarbons in the feed. Where reaction of vinyl olefins only is desired, feed olefins may contain up to about 25 mol percent or more, preferably 15 mol percent or less, of each of internal and vinylidene olefins. Where the reaction of internal or vinylidene olefins is desired, there is no limit to the proportions of the olefins of the various types.

Various sources of bisulfite ion may be used in the present reaction. Bisulfite or metabisulfite such as ammonium bisulfite, sodium bisulfite, potassium bisulfite, lithium bisulfite, sodium metabisulfite, potassium metabisulfite and other alkali metal bisulfites or metabisulfites may be fed as such singly or in admixture and the pH adjusted to the desired initial value by the addition of a suitable base such as ammonium or alkali metal oxide or hydroxide, preferably a base whose cations correspond to those of the bisulfite or metabisulfite or combination thereof used.

In addition, sulfites having cations as set forth in the preceding paragraph for the bisulfites and metabisulfites may be fed and the pH adjusted to the desired initial range by the feed of suitable acidic substance such as $SO_2$, HCl or bisulfite or metabisulfite of the preceding paragraph having similar or different cation. In addition, suitable bisulfite is obtained by feeding a suitable base as set forth in the preceding paragraph and adding suitable acidic substance to bring the initial pH to the desired level. Thus NaOH, for example, may be reacted with $SO_2$ to provide a bisulfite system of the desired pH in which case approximately 85 percent of the bisulfite will be present in the initial system and the remaining 15 percent of the bisulfite being generated in the course of the reaction by the addition of $SO_2$ required to maintain the pH in the specified range of 5.0 to 8.0.

The pH requirementss set forth herein in general impose the limitation that the starting system be no more acid than about 5.0. Such a system is readily obtained in one or more of several ways.

A preferred way to obtain the bisulfite reactant and a system pH in the range specified is to prereact hydroxide with $SO_2$. Simple routine experimentation indicates the amount of base and $SO_2$ to be used to put the initial system pH in the specified range so that as the reaction progresses, the system pH can be maintained in the specified pH range by the further addition of $SO_2$. In general, it is preferred to have a starting pH near the lower end of the range, typically from about 5 to about 7.0 so that, as the pH rises in the course of the reaction, the pH can be held in the specified range of from about 5 to about 8, or preferably not in excess of about 7.5 by the addition of $SO_2$. These preferred conditions usually result in the presence initially of from about 75 to about 95 percent of the total sulfur required for the reaction, the balance of 5 to 25 percent of the sulfur required being added during the course of the reaction preferably in the form of gaseous $SO_2$ bubbled into the reaction mass to maintain the desired system pH. System pH can be measured in various ways. As an example, a sample may be withdrawn and its pH determined using a suitable indicator as is well known to those skilled in the art. Preferably, to save the time and the delay involved in withdrawing and examining samples using an indicator, it is preferred to insert a glass electrode into the reaction system and to read the pH in the aqueous phase by a direct reading meter. Very close pH measurement and control is thus facilitated with a minimum of operator effort and the meter may be used to control directly and automatically the admission of $SO_2$ into the system. Generally speaking, this operation is far less time consuming than a process which limits the initial amount of bisulfite to about 25 mol percent of the olefin charged and adds bisulfite during the course of the reaction.

The total amount of bisulfite provided for the present reaction depends upon several factors. In general, one desires enough bisulfite to react with the reactive olefinic bonds in a reasonable reaction time and at the same time to avoid an excess of bisulfite that remains in the product as undesired inorganics. The product usually is a mixture wherein some molecules contain one atom of sulfur and some molecules contain two atoms of sulfur. When one uses large percentages of solvents the product contains about 1.25 atoms of sulfur per molecule of product. When one uses lesser amounts of solvents relative to the olefins and bisulfite, the product usually contains more sulfur per molecule of product, up to about 1.5 atoms or more of sulfur per molecule of product. To react out all of the bisulfite and olefin in reasonable reaction times of from about 2 to about 8 hours, usually it is preferred to provide about 1.4 gram atoms of sulfur per gram mol of reactive olefin and to operate with preferred amounts of solvent as set forth hereinafter.

Although the use of large amounts of bisulfite relative to olefin may shorten reaction time and enhance the overall conversion of the olefin, it is usually preferred to avoid large excesses of bisulfite to minimize residual inorganic material in the product sulfonate. Thus ratio of mols of bisulfite used per mol of reactive olefin preferably is from 1:1 to about 1.7:1, preferably from about 1:1 to about 1.5:1, especially from about 1.30:1 to about 1.45:1.

For optimum yield and minimum production of undesired sulfate by-products, precautions preferably are taken to avoid oxidation of bisulfite or sulfite to sulfate both before and during the reaction with olefin. Preferably therefore, hydroxide and bisulfite are handled in such a way as to avoid contact thereof with oxygen. Thus, reflux condensers, reaction vessels and lines containing bisulfite or the precursor hydroxide and $SO_2$ preferably are purged with nitrogen prior to the reactions and free oxygen is excluded during the bisulfite addition reaction.

Suitable solvent or diluent systems for the present process are somewhat limited. Suitable solvent systems contain water plus one or more lower alkanols having from 2 to about 4 carbon atoms per molecule. Preferred lower alkanol for such systems is isopropanol. Ethanol is also a suitable co-solvent; however, usually it is less preferred than isopropanol because of handling, storage and related problems. Other suitable alkanols are normal propanol, normal butanol, and isobutanol. Although useful, the other butanols are less preferred. The weight ratio of alkanol to water for the co-solvent system is from about 1:4 to about 3:1, preferably from about 1:3 to about 1:1, typically about 2:3.

The weight percent of solvent (water plus alcohol) is from about 70 to about 95 of the reaction system or mass, preferably from about 75 to about 85, typically about 80.

The solvent proportions have a significant effect upon the reaction rate. Systems which contain from about 70 to 85 percent of solvent are usually preferred for fast reaction rate and efficient utilization of reactor volume. Above 85 percent of solvent, the reactor utilization is generally undesirably small. With less than 50 percent solvent, the reaction rate becomes undesirably slow for commercial scale operations and the products have a high percentage of molecules with two sulfur atoms each.

Although various initiators have different effects upon rates, the various initiators described in the prior art for use in the bisulfite addition to olefinic double bonds are in general useful in the present process. Initiators may be used individually or, if preferred, in compatible combinations to provide progressive effectiveness over the entire reaction period since some initiators are slow to reach their maximum effectiveness in the reaction while others reach maximum effectiveness rapidly and may decline in effectiveness before all the olefin reacts. Generally speaking, one prefers to avoid the complications of using two initiators or of multiple injections of the same initiator by choosing an initiator that has a broad peak of effectiveness under the conditions selected for operation. Various suitable initiators include soluble nitrates, nitrites, peroxides, inorganic peroxides, organic peroxides, organic peresters, organic hydroperoxides and organic azo-nitriles. Typical initiators include sodium nitrate and cumene hydroperoxide. Preferred initiators are the organic peroxides, including the alkyl peroxides, aryl peroxides and aryl hydroperoxides. Especially preferred are the organic peresters, such as tertiary butyl perbenzoate, tertiary butyl peracetate, and t-butyl peroctanoate. Other useful initiators are azo-bis isobutyronitrile, sodium nitrite, and the like. Other initiators are disclosed in U.S. Pat. Nos. 2,504,411 and 3,479,397, pertinent portions of which are herewith incorporated herein by reference.

The amount of initiator used is an effective amount for the reaction. In practice this ranges from about 0.01 to about 0.05 mols of initiator per mol of olefin, preferably from about 0.01 to about 0.03 mols of initiator per mol of olefin. In general, one uses enough initiator to achieve a practical reaction rate but avoids the use of more initiator than is necessary. The amount of initiator desirable is readily determined by routine experimentation. For example, about 1 mol percent of tertiary butyl perbenzoate, (based on the reactive olefin fed) may be added initially. Additional amounts of initiator may be added progressively if desired to establish a desired reaction rate. Although undesirable as a routine matter, the addition of initiator during the course of reaction is not difficult experimentally particularly where operation is at atmospheric pressure using a reflux condenser. When the optimum amount of initiator is determined by routine experimentation, subsequent runs are usually conducted with a single, initial, charge of catalyst.

Preferably the reaction is conducted at reflux temperatures which provide autogenous pressure of from about ½ to about 10 atmospheres. Operation at atmospheric pressure or at higher pressures is usually preferred to provide fast reaction rate and avoid the need for a vacuum system. On the other hand, pressures higher than about 100 psig usually are not necessary to achieve a rapid reaction and hence are usually avoided by selection of appropriate operating temperatures, alkanols, etc.

Although important for matters such as rate, temperature is not a critical factor. Generally, the temperature is established on a basis of pressure considerations such as the partial pressures of the components and a general preference for an operating pressure of from about 0 to about 100 psig to avoid special precautions for vacuum or high pressure operation. Typical reaction temperatures are from about 25° to about 200°C, preferably from about 40° to about 120°C for most of the lower alcohol containing solvent systems. Typical temperatures for isopropyl alcohol-water solvents systems refluxing at atmospheric pressure is from about 80° to about 90°C.

The product of the reaction is typically a mixture of alkane sulfonates [$RCH_2CH_2SO_3Na$] and alkane sulfinate-sulfonates [$RCH(SO_2Na)CH_2SO_3Na$]. The product typically is composed of from about 25 to about 50 mol percent of the latter component corresponding to from about 1.25 to about 1.50 gram atoms of sulfur per gram mol of product. The factors governing the proportions have been discussed in detail in the foregoing.

The following examples indicate preferred embodiments and aspects of the present invention.

EXAMPLE I 25.1 Grams (615 millimols) of NaOH (98 percent) was dissolved in 300 ml of distilled water under a nitrogen blanket in a 1 liter three neck creased flask equipped with heater, stirrer, reflux condenser, combination electrode and meter for pH measurement, and a thermometer. $SO_2$ was added to the NaOH solution at the rate of 1.10 grams/min. (~17.2 mmols/min.) for 30 min., at the end of which time 33–34 grams $SO_2$ (~0.52 mols) had been absorbed (and the pH had decreased to 5.7 at 60°–65°C). This was about 85 percent of the $SO_2$ required for complete conversion of the hydroxide all the way to bisulfite. To this was added 84.0 grams (0.50 mols) of a mixture of $C_{10}$, $C_{12}$ and $C_{14}$ olefin (25, 50, 25 wt. percent respectively) (91.1 percent vinyl olefin 0.42 mols) dissolved in 300 ml isopropanol (236 grams) containing 1.5 grams (0.773 millimols) of tertiary butyl perbenzoate catalyst. The pH of the resulting mixture was 6.05.

The mixture was heated under nitrogen to reflux at atmospheric pressure. The temperature was about 82°C. After about ½ hour, the pH began to drift upward. Gaseous $SO_2$ was bubbled into the reaction mixture when the pH rose to 7.2 and was subsequently added as necessary to maintain a pH of about 6.9. After about 2½ hours from the start of the heating, the mixture became homogeneous. After about 3½ hours from the start, the pH became stabilized at about 6.8 without requiring further addition of $SO_2$. At this point 72 g of the olefin had reacted for a vinyl olefin conversion of 94 percent.

The product was recovered by evaporating the solvent and unreacted olefin.

The reaction product weighed 128 grams, contained about 1.4 wt. percent $H_2O$, less than 1 wt. percent unreacted inorganic material and 14.6 wt. percent S on an anhydrous basis. The product therefore was about 62 mol percent (55 wt. percent) Na monosulfonate salts and about 38 mol percent (45 wt. percent) Na sulfinate-sulfonate salts and has a S/chain value of 1.38.

EXAMPLES II–V

Example I was repeated in a series of similar runs using various olefins and catalysts with 300 ml of $H_2O$ and 300 ml of isopropanol. Catalysts used were tertiary butyl perbenzoate or a mixture of tertiary butyl perbenzoate (TBPB) and tertiary butyl peracetate (TBPA) in various proportions.

Data are tabulated in Table I.

EXAMPLES VI–XII

Example I was repeated in a series of similar runs using dodecenes in various combinations of amounts of solvents and NaOH. The data in Table II show the effect of various ratios of solvents and of pH upon reaction rate, conversion and ratio of gram atoms of sulfur per gram mol of product. In these runs, $SO_2$ was added as necessary to achieve the indicated initial and average pH values. The dodecenes used contained approximately 93.8 percent dodecene-1.

TABLE I

| Run No. | Olefin Used | Percent Vinyl | g Olefin Total | g Vinyl Olefin | Cat., g TBPB | Cat., g TBPA | NaOH mmoles | $SO_2$ mmoles Initial | $SO_2$ mmoles Total | Olefin Reacted g |
|---|---|---|---|---|---|---|---|---|---|---|
| 2 | $C_{10/12/14}$ (as in Ex. I) | 91.1 | 94.00 | 85.63 | 1.0 | 1.5 | 613 | 342 | 619 | 73.0 |
| 3 | $C_{12}$ | 94.3 | 88.00 | 82.98 | 1.0 | 0.5 | 618 | 459 | 565 | 72.2 |
| 4 | $C_{12}$ | 94.3 | 80.00 | 75.44 | 1.5 | — | 618 | 481 | 563 | 68.8 |
| 5 | $C_{12}$ | 94.3 | 80.00 | 75.44 | 1.5 | — | 618 | 528 | 620 | 71.3 |

TABLE II

| Run No. | NaOH g | NaOH moles | i-PrOH ml | $H_2O$, ml | g NaOH/ g $H_2O$ | Olefin Feed, g Total | Olefin Feed, g Vinyl | pH Range Initial | pH Range Avg. | Total Time, Hrs. | Vinyl Conv. g | Vinyl Conv. % | Product Sulfur/Molecule |
|---|---|---|---|---|---|---|---|---|---|---|---|---|---|
| 6 | 25.0 | 0.625 | 300 | 280 | 0.089 | 82 | 77 | 6.8 | 7.1–7.3 | 3 | | | 1.27 |
| 7 | 37.5 | 0.95 | 150 | 450 | 0.083 | 120 | 113 | 6.2 | 6.8–6.9 | 7 | 75.3 | 67 | 1.40 |
| 8 | 37.5 | 0.95 | 450 | 300 | 0.125 | 120 | 113 | 6.2 | 6.8–7.4 | 6 | 85.4 | 76 | 1.47 |
| 9 | 12.5 | 0.31 | 300 | 300 | 0.041 | 40 | 38 | 6.8 | 6.8 | 3 | 35.4 | 93 | 1.32 |
| 10 | 50.0 | 1.25 | 300 | 300 | 0.167 | 150 | 141 | 5.8 | 6.8–7.0 | 7 | 117.2 | 83 | 1.50 |
| 11 | 50.0 | 1.25 | 300 | 300 | 0.167 | 150 | 141 | 6.6 | 8.0–8.5 | 48 | 74.8 | 53 | 1.29 |
| 12 | 12.5 | 0.31 | 300 | 300 | 0.041 | 40 | 38 | 7.7 | 8.0–8.1 | 24 | 32.9 | 87 | 1.07 |

We claim:

1. A process for preparing alkyl sulfonate salts which comprises reacting from about 1.0 to about 1.7 mols of aqueous ammonium or alkali metal bisulfite with about 1.0 mols of straight chain terminal olefin having from about 8 to about 30 carbon atoms per molecule in the presence of lower alkanol having from 2 to about 4 carbon atoms per molecule and an effective amount of a reaction initiating agent, at a pH of from about 5 to about 8, at a temperature of from about 25° to about 200°C, the reaction system containing from about 70 to about 95 wt. percent of water and lower alkanol, the weight ratio of alkanol to water ranging from about 1:4 to about 3:1, the initial pH of the reaction mixture being from about 5 to about 8, $SO_2$ being fed to the system as the reaction progresses to maintain a selected pH of from about 5 to about 8, said process being conducted in the absence of free oxygen.

2. The process of claim 1 wherein the amount of the water and lower alkanol is from about 75 to about 85 weight percent of the reaction system.

3. The process of claim 1 wherein the amount of the water and lower alkanol is about 80 percent.

4. The process of claim 1 wherein the weight ratio of alkanol to water is from about 1:3 to about 1:1.

5. The process of claim 1 wherein the weight ratio of alkanol to water is about 2:3.

6. The process of claim 1 wherein the mol ratio of bisulfite to olefin is from about 1:1 to about 1.50:1.

7. The process of claim 1 wherein the mol ratio of bisulfite to olefin is from about 1.30:1 to about 1.45:1.

8. The process of claim 1 wherein the temperature is from about 40° to about 120°C.

9. The process of claim 1 wherein the temperature is from about 80° to about 90°C.

10. The process of claim 1 wherein the initiator is an organic peroxide.

11. The process of claim 1 wherein the initiator is a tertiary alkyl perester.

12. The process of claim 1 wherein the initiator is a tertiary alkyl perbenzoate.

13. The process of claim 1 wherein the initiator is tertiary butyl perbenzoate.

14. The process of claim 1 wherein the initiator is a tertiary alkyl peracetate.

15. The process of claim 1 wherein the initiator is tertiary butyl peracetate.

16. The process of claim 1 wherein the bisulfite is sodium bisulfite, sodium metabisulfite or ammonium bisulfite, or a mixture thereof.

17. The process of claim 1 wherein the bisulfite is a mixture of sodium bisulfite and sodium metabisulfite.

18. The process of claim 1 wherein the pH is from about 6 to about 7.5.

19. The process of claim 1 wherein the initial pH is from about 5 to about 7 and the $SO_2$ is added to maintain a pH not in excess of about 7.5.

20. The process of claim 1 wherein substantially all of the initial reactants, the water, the initiator and the alkanol are combined and then the system is heated to reflux at the selected temperature.

21. A process for preparing alkyl sulfonate salts which comprises producing a reaction mixture containing the addition product of ammonium or alkali metal bisulfite and straight chain terminal olefins having from about 8 to about 30 carbon atoms per molecule, reaction initiating agent, water, and lower alkanol having from 2 to about 4 carbon atoms per molecule, the system containing from about 70 to about 95 wt. percent of water and lower alkanol, the weight ratio of alkanol to water ranging from about 1:4 to about 3:1, withdrawing intermittently or continuously a portion of the reaction mixture, and replacing the withdrawn reaction mixture with additional bisulfite, olefin, water, alcohol and reaction initiating agent to maintain said proportions of bisulfite while maintaining a pH of from about 5 to about 8 and a temperature of from about 25° to about 200°C by the addition of $SO_2$, said process being conducted in the absence of free oxygen.

22. The process of claim 21 wherein the withdrawal and replacement are proportioned to maintain a homogeneous system.

* * * * *